(12) United States Patent
Kubicek et al.

(10) Patent No.: US 7,473,809 B2
(45) Date of Patent: Jan. 6, 2009

(54) METHOD OF PREPARING DICHLOROPROPANOLS FROM GLYCERINE

(75) Inventors: Pavel Kubicek, Decin (CZ); Petr Sladek, Sebuzin (CZ); Ivana Buricova, Usti nad Labem (CZ)

(73) Assignee: Spolek pro chemickou a hutni vyrobu, Usti nad Labem (CZ)

( * ) Notice: Subject to any disclaimer, the term of this patent is extended or adjusted under 35 U.S.C. 154(b) by 48 days.

(21) Appl. No.: 10/570,155

(22) PCT Filed: Aug. 23, 2004

(86) PCT No.: PCT/CZ2004/000049

§ 371 (c)(1),
(2), (4) Date: Dec. 26, 2006

(87) PCT Pub. No.: WO2005/021476

PCT Pub. Date: Mar. 10, 2005

(65) Prior Publication Data

US 2007/0167659 A1     Jul. 19, 2007

(30) Foreign Application Priority Data

Sep. 1, 2003   (CZ)   ............. PV 2003-2346

(51) Int. Cl.
*C07C 31/34*   (2006.01)

(52) U.S. Cl. ...................... 568/841; 568/852
(58) Field of Classification Search ............ 568/841, 568/852
See application file for complete search history.

(56) References Cited

U.S. PATENT DOCUMENTS

| 2,144,612 A | 1/1939 | Britton et al. |
| 2,198,600 A | 4/1940 | Britton et al. |
| 6,072,076 A | 6/2000 | Schmidt et al. |

FOREIGN PATENT DOCUMENTS

| EP | 0 781 760 | 7/1997 |
| JP | 03-056430 | 3/1991 |
| WO | 02/50014 | 6/2002 |

*Primary Examiner*—Sikarl A Witherspoon
(74) *Attorney, Agent, or Firm*—Oblon, Spivak, McClelland, Maier & Neustadt, P.C.

(57) ABSTRACT

A method of highly selective catalytic hydrochlorination of glycerine and/or monochloropropanediols to the dichloropropanol products 1,3-dichloro-2-propanol and 2,3-dichloro-1-propanol, carried out in at least one continuous reaction zone at reaction temperatures in the range of 70-140° C. and with continuous removing of the water of reaction, the liquid feed containing at least 50% by weight of glycerine and/or monochloropropanediols. The method can be carried out in a continuously operating one-step circulation reactor or a cascade of continuous flow reactors of the liquid-gas type.

21 Claims, No Drawings

METHOD OF PREPARING DICHLOROPROPANOLS FROM GLYCERINE

TECHNICAL FIELD

This invention relates to the technology of production of epichlorohydrin, the field of chemical engineering. Epichlorohydrin is an important raw material for the production of epoxide resins, synthetic elastomers, sizing agents for papermaking industry and the like.

BACKGROUND ART

In the industrial production of epichlorohydrin, a technology is mostly worldwide used, which comprises:
- high temperature radical substitutive chlorination of propene to allyl chloride;
- preparation of dichloropropanols by addition of hypochlorous acid to allyl chloride; and
- dehydrochlorination of dichloropropanols with an alkali aqueous solution to epichlorohydrin.

The basic features of this technology are, above all:
- relatively mediocre total yield of the synthesis based on the starting propylene of ca. 73%;
- low yield of the synthesis based on chlorine of ca. 38%;
- high unit consumption of energy;
- high unit volume of waste water of ca. 35 $m^3/t$ of epichlorohydrin, pollution AOX (Adsorbable Organic Halides), DIS (Dissolved Inorganic Salts) and COD (Chemical Oxygen Demand); and
- use of hazardous propene and evaporated chlorine in the process.

The technology of Showa-Denko (e.g., U.S. Pat. Nos. 5,011,980, 5,227,541 or 4,634,784), comprising:
- palladium-catalyzed oxidation of propene with acetic acid to allyl acetate;
- catex-catalyzed hydrolysis of allyl acetate to allyl alcohol;
- catalytic chlorination of allyl alcohol to dichloropropanol; and
- alkaline dehydrochlorination of dichloropropanol to epichlorohydrin is worldwide used to only minor extents.

In both cases, the basic starting materials are propene, chlorine and an alkali, for example calcium hydroxide or sodium hydroxide.

Accordingly, for economic, environmental, and safety reasons, new synthetic routes are being sought worldwide. For several years, attempts have been made to manage a process of direct catalytic oxidation of allyl chloride to epichlorohydrin with hydrogen peroxide, or organic hydroperoxides, with use of catalysts based on titanium silicalites (e.g., U.S. Pat. Nos. 5,466,835, 6,187,935, 6,288,248, or 6,103,915) but without any commercial application to date.

One of further possible synthetic routes has been known since the beginning of the $20^{th}$ century; its principle resides in catalytic hydrochlorination of glycerine by means of anhydrous hydrogen chloride according to the German patent to Boehringer, C. F. und Söhne, Waldhof b. Mannheim: Verfahren zur Darstellung von Mono- und Dichlorhydrin aus Glycerin und gasformiger Salzsäure, DE Patent No. 197308, 1906.

The principle is a reaction of glycerine with hydrogen chloride in the presence of carboxylic acids as catalysts, providing 1,3-dichloro-2-propanol and water. The said reaction is carried out in the liquid phase under temperatures of around 100° C. Pressure can be either atmospheric or elevated, for increasing the solubility of gaseous HCl in the reaction mixture. An optimal concentration of the homogeneous acetic acid catalyst is ca. 1-2% by weight; at higher concentrations undesired by-products are formed to a greater extent, which lower the yields. Besides acetic acid, the Patent mentions other carboxylic acids, propionic acid having been tested. The published yield of the batch arrangement without separation of water amounts to, in a control recalculation, ca. 75%. In order to increase the yield and reduce the hydrogen chloride loss a basic problem is removal of the water of reaction for shifting the equilibrium towards emerging dichloropropanol.

U.S. Pat. No. 2,144,612 has tried to solve the problem of sufficient removal of the reaction water at a suitable reaction temperature by the use of various kinds of inert, water immiscible solvents such di-n-butyl ether, ethylene dichloride, propylene dichloride or chlorobenzol, which allow to remove the reaction water as an acid distillate. The patent mentions that only the little amount of residues is formed, the reaction may be readily carried to completion, the solution of glycerol-dichlorohydrin obtained as a reaction product is substantially free from water and loss of glycerol-dichlorohydrin in hardly separable aqueous acid solution is minimized. Also the higher content of catalyst in range of 5% based on glycerine input is mentioned.

U.S. Pat. No. 2,198,600 has tried to solve the problem of the purification and the recovery of dichloropropanol from acid distillate by extraction using a suitable organic solvent for dichloropropanol, preferably di-n-butyl ether.

All the above mentioned methods described in the respective patents were developed as discontinuous batch processes.

In industrial scale such methods are not feasible for high losses of hydrogen chloride, the necessity of several batch reaction steps with long residence times of the order of hours to tens of hours, and hence high demands on the size of apparatuses, the logistics of raw materials and products, sanitation of waste streams, labour hygiene and the like. Also the use of significant portion of inert solvents required for the suitable results acceptable in the industrial scale significantly increases the reactor volumes and needs a lot of additional equipments for solvents handling, treatment, recovery etc.

For these reasons a method of continuous preparation of a mixture of 1,3-dichloro-2-propanol and/or 2,3-dichloro-1-propanol, characterized by high conversion of the starting materials, high yields of the products and high selectivity of the reaction system has been developed.

DISCLOSURE OF INVENTION

This invention consists in a method of preparing the dichloropropanols 1,3-dichloro-2-propanol and 2,3-dichloro-1-propanol by hydrochlorination of glycerine and/or monochloropropanediols with gaseous hydrogen chloride with catalysis of a carboxylic acid, wherein said hydrochlorination is carried out in at least one continuous reaction zone at reaction temperatures in the range of 70-140° C. and with continuous removing of the water of reaction, the liquid feed containing at least 50% by weight of glycerine and/or monochloropropanediols.

This method does not need any additional compounds like solvents to reach industrially acceptable yields. The mixture of products, which apart from dichloropropanols contains also the reaction water and the small amount of catalyst acetic acid and unreacted hydrogen chloride, can be favourably used without any treatment for the next reaction step in epichlorohydrin synthesis, e.g. for the alkaline dehydrochlorination.

Preferably, the liquid feed contains 80-100% by weight of glycerine, and the carboxylic acid catalyst is preferably acetic acid.

The reaction temperature is preferably 100-110° C.

The hydrochlorination can be carried out in a continuously operating one-step circulation reactor or in a cascade of continuous flow reactors of the liquid-gas type.

For achieving favourable conversions of the starting glycerine to the dichloropropanol product it is also necessary, apart from the presence of a catalyst, to remove the water of reaction from the reaction environment for the reason of chemical equilibrium, preferably by distillation under reduced pressure.

In case of a circulation reactor, the raw materials glycerine, hydrogen chloride and the acetic acid catalyst can be fed into external circulation upstream the reactor itself and, for primary collection of the dichloropropanol product and the water of reaction, a distillation device can be located in the circulation, preferably a distillation column operated at reduced pressure. The remaining balance of the reaction mixture can be also secondarily collected from the circulation and, after recovery of the dichloropropanol product and the monochloropropanediol reactive intermediate, which are returned to the reaction, the residue containing a mixture of undesired products is further processed. The recovery can be advantageously carried out by distillation under reduced pressure, wherein the undesired higher-boiling waste products leave as the distillation residue.

By balancing the set of parameters of the circulation reactor such as the ratio between the quantity of reactor circulation and glycerine input, the ratio between the quantity of the secondary collection and glycerine input, the reactor temperature, the value of reduced pressure in the continuous primary distillation in the reactor circulation, etc., optimization of the process and its yields can be achieved.

In case of a cascade of the continuous flow reactors the number of members of the cascade can range from one to five, preferably three. The raw materials glycerine, hydrogen chloride and the acetic acid catalyst are fed into the first member of the cascade; hydrogen chloride and a supplement for the loss of the catalyst are in turn fed into the other members. Distillation of the water of reaction is always located between the individual members of the cascade. After distilling off the water of reaction and a part of the dichloropropanol product the distillation residue is subjected to hydrochlorination in the next member of the cascade. It is advisable, for increasing the total yield, to recover dichloropropanols and the reactive intermediates monochloropropanediols from the distillation residue after distilling off the water of reaction and dichloropropanol from the last member of the cascade. The recovery can preferably be carried out by distillation under reduced pressure, wherein higher boiling waste products are separated as the distillation residue and the distillate is dichloropropanols and monochloropropanediols, recycled back to the reactor, preferably into the first member of the cascade.

Generally, any reactor for the reaction of the liquid-gas type can be chosen for the reaction itself, such as a stirrer reactor, a bubble tower (column), variously filled columns for the liquid-gas contact, ejector reactors and the like.

For dispersing the gaseous hydrogen chloride, any dispersing means can be used, such as nozzles, perforated plates or pipes, microporous plates, ejectors and the like.

Pressures in the reactors can be atmospheric, or elevated for better solubility of hydrogen chloride in the reaction mixture. Temperatures in the reactors can range between 70 and 140° C., preferably 100-110° C.

The total mean residence time of the system can be selected in the range of 5-40 hours according to the required total conversion of glycerine and total yield of the dichloropropanol product.

For the distillation under reduced pressure to separate the water of reaction any device for distillation can be used, such as evaporators of various constructions with or without a source of heat, rectification columns with various internals such as trays, structured packing, random packing and the like.

As devices for recovery distillation, generally known apparatuses for distillation can be used, such as various types of evaporators or distillation systems.

Starting material glycerine can be of various quality with the various glycerine content and various kinds of the impurities. Distilled glycerine with the various contents of glycerine can be used; content of 90.0-99.9% being preferred. Also crude glycerine with various contents of glycerine can be used; content of 80.0-90.0% being preferred.

Alternatively, the glycerine feed can be, partially or totally, replaced by monochloropropanediol (especially 3-chloro-1, 2-propanediol, and/or 2-chloro-1,3-propanediol), optionally prepared by other methods, such as hydrochlorination of glycerine with a solution of hydrochloric acid.

EXAMPLES

Example 1

According to the described disclosure of the invention the following experiment was conducted. In a circulation column reactor, consisting of a vertical cylinder with external circulation of the reaction mixture, a feed of glycerine, containing 97.5% of glycerine, 2% of acetic acid and 0.5% of water, was fed into the external circulation upstream the reactor itself in the amount of 5.0 kg/h. Gaseous hydrogen chloride was fed directly into the bottom of the reactor through classical dispersing devices in the amount of 4.6 kg/h. In the external circulation there was inserted a vacuum rectification column downstream the reactor; a mixture of the dichloropropanol product, the reaction water and the residual hydrogen chloride was collected as the distillate in the amount of 9.3 kg/h. The distillation residue was pumped back to the reactor. The residual balance of the reaction mixture was also collected from the circulation downstream the rectification column in the amount of 1.4 kg/h and this was subjected to vacuum distillation in an evaporator in order to recover the dichloropropanol product and the monochloropropanediol reactive intermediate, which were returned back to the reaction in the amount of 1.2 kg/h together with the glycerine feed. The distillation residue from the recovery, containing a mixture of undesired products, was collected as waste in a tank. The basic parameters and results are illustrated in the following Table:

| Parameter | |
|---|---|
| Reaction temperature | 106° C. |
| Pressure in the reactor | 101 kPa |
| Conversion of glycerine | 99.8% |
| Yield of 1,3-dichloro-2-propanol + 2,3-dichloro-1-propanol | 95.6% |

Example 2

According to the described disclosure of the invention the following experiment was conducted. A cascade of continuous flow reactors with 3 reactors of the cascade without final recovery of the monochloropropanediol reactive intermediate was sequentially modelled. A feed of glycerine, containing 97.5% of glycerine, 2% of acetic acid and 0.5% of water, was continuously fed into the first member of the cascade—a tower reactor of the liquid-gas type; as was hydrogen chloride through classical dispersing devices. The product, containing a mixture of dichloropropanols, monochloropropanediols and other side products, was collected into a tank. After the selected time of continuous run the reaction was interrupted; the product was subjected to one-step equilibrium vacuum distillation to distil off the reaction water, a part of dichloropropanol and excess hydrogen chloride. The distillation residue was then used as injection into the next member of the sequentially designed cascade. The distillates together with the reaction mixture from the last member of the cascade were the output of the whole system. The basic parameters and results of the 3-member cascade are illustrated in the following Table:

| Parameter | |
|---|---|
| Reaction temperature | 95° C. |
| Pressure | 101 kPa |
| Conversion of glycerine | 99.9% |
| Yield of 1,3-dichloro-2-propanol + 2,3-dichloro-1-propanol | 83.1% |

Example 3

According to the described disclosure of the invention the following experiment was conducted. In a circulation column reactor, consisting of a vertical cylinder with external circulation of the reaction mixture, a feed of glycerine, containing 88.7% of glycerine, 2% of acetic acid and 9.3% of water was fed into the external circulation upstream the reactor itself in the amount of 5.4 kg/h. Gaseous hydrogen chloride was fed directly into the bottom of the reactor through classical dispersing devices in the amount of 4.3 kg/h. In the external circulation there was inserted a vacuum rectification column downstream the reactor; a mixture of the dichloropropanol product, the reaction water and the residual hydrogen chloride was collected as the distillate in the amount of 9.3 kg/h. The distillation residue was pumped back to the reactor. The residual balance of the reaction mixture was also collected from the circulation downstream the rectification column in the amount of 1.4 kg/h and this was subjected to vacuum distillation in an evaporator in order to recover the dichloropropanol product and the monochloropropanediol reactive intermediate, which were returned back to the reaction in the amount of 1.1 kg/h together with the glycerine feed. The distillation residue from the recovery, containing a mixture of undesired products, was collected as waste in a tank. The basic parameters and results are illustrated in the following Table:

| Parameter | |
|---|---|
| Reaction temperature | 107° C. |
| Pressure in the reactor | 101 kPa |
| Conversion of glycerine | 99.6% |
| Yield of 1,3-dichloro-2-propanol + 2,3-dichloro-1-propanol | 90.9% |

Example 4

According to the described disclosure of the invention the following experiment was conducted. In a circulation column reactor, consisting of a vertical cylinder with external circulation of the reaction mixture, a feed of crude glycerine, containing 84.9% of glycerine, 2% of acetic acid, 4.7% of water and 8.4% of non-volatile compounds, was fed into the external circulation upstream the reactor itself in the amount of 5.5 kg/h. Gaseous hydrogen chloride was fed directly into the bottom of the reactor through classical dispersing devices in the amount of 4.5 kg/h. In the external circulation there was inserted a vacuum rectification column downstream the reactor; a mixture of the dichloropropanol product, the reaction water and the residual hydrogen chloride was collected as the distillate in the amount of 8.9 kg/h. The distillation residue was pumped back to the reactor. The residual balance of the reaction mixture was also collected from the circulation downstream the rectification column in the amount of 2.0 kg/h and this was subjected to vacuum distillation in an evaporator in order to recover the dichloropropanol product and the monochloropropanediol reactive intermediate, which were returned back to the reaction in the amount of 1.0 kg/h together with the glycerine feed. The distillation residue from the recovery, containing a mixture of undesired products, was collected as waste in a tank. The basic parameters and results are illustrated in the following Table:

| Parameter | |
|---|---|
| Reaction temperature | 103° C. |
| Pressure in the reactor | 101 kPa |
| Conversion of glycerine | 99.5% |
| Yield of 1,3-dichloro-2-propanol + 2,3-dichloro-1-propanol | 89.3% |

The invention claimed is:

1. A method of preparing 1,3-dichloro-2-propanol and 2,3-dichloro-1-propanol comprising hydrochlorinating glycerine with gaseous hydrogen chloride with catalysis of a carboxylic acid, wherein said hydrochlorination is carried out solvent-free in at least one continuous reaction zone at reaction temperatures in the range of 70-140° C. and with continuous removing of the water of reaction by distillation at reduced pressure, a liquid feed containing at least 50% by weight of glycerine.

2. The method according to claim 1, wherein the liquid feed contains 80-100% by weight of glycerine.

3. The method according to claim 1, wherein the catalysis is made with acetic acid.

4. The method according to claim 1, wherein the reaction is carried out at a temperature of 100-110° C.

5. The method according to claim 1, wherein the distillation at reduced pressure is carried out in a rectification zone linked to the reaction zone.

6. The method according to claim 5, wherein the method comprises removing of the water of reaction by distillation and at least partial primary collection of the 1,3-dichloro-2-propanol and 2,3-dichloro-1-propanol product.

7. The method according to claim 6, wherein secondary collection is made, from which dichloropropanols and monochloropropanediols are recycled to the process.

8. The method according to claim 7, wherein the secondarily collected residual balance of the reaction mixture is subjected to distillation under reduced pressure in order to separate the higher boiling waste products as the distillation residue and the dichloropropanols and monochloropropanediols, recycled to the reactor, as the distillate.

9. The method according to claim 1, wherein the method is carried out in a cascade of continuous flow reaction zones wherein the water of reaction is collected, together with partial collection of the product dichloropropanols, by distillation at reduced pressure, located always downstream the individual reaction zones of the cascade, and the distillation residue is fed into the next zone of the cascade.

10. The method according to claim 9, wherein the reaction mixture exiting from the last step of the cascade is subjected to a two-step distillation, wherein in the first step the water of reaction is separated together with the dichloropropanol reaction product as the distillate and in the second step the higher boiling waste products are separated as the distillation residue and the dichloropropanols and monochloropropanediols are separated as the distillate and are recycled back to the process, preferably into the first step of the cascade.

11. A method of preparing 1,3-dichloro-2-propanol and 2,3-dichloro-1-propanol comprising hydrochlorinating monochloropropanediols with gaseous hydrogen chloride with catalysis of a carboxylic acid, wherein said hydrochlorination is carried out solvent-free in at least one continuous reaction zone at reaction temperatures in the range of 70-140° C. and with continuous removing of the water of reaction by distillation at reduced pressure, a liquid feed containing at least 50% by weight of monochloropropanediol.

12. The method according to claim 11, wherein said monochloropropanediol is 2-chloro-1,3-propanediol.

13. The method according to claim 11, wherein said monochloropropanediol is 3-chloro-1,2-propanediol.

14. The method according to claim 11, wherein the catalysis is made with acetic acid.

15. The method according to claim 11, wherein the reaction is carried out at a temperature of 100-110° C.

16. The method according to claim 11, wherein the distillation at reduced pressure is carried out in a rectification zone linked to the reaction zone.

17. The method according to claim 16, wherein the method comprises removing of the water of reaction by distillation and at least partial primary collection of the 1,3-dichloro-2-propanol and 2,3-dichloro-1-propanol product.

18. The method according to claim 17, wherein secondary collection is made, from which dichloropropanols and monochloropropanediols are recycled to the process.

19. The method according to claim 18, wherein the secondarily collected residual balance of the reaction mixture is subjected to distillation under reduced pressure in order to separate the higher boiling waste products as the distillation residue and the dichloropropanols and monochloropropanediols, recycled to the reactor, as the distillate.

20. The method according to claim 11, wherein the method is carried out in a cascade of continuous flow reaction zones wherein the water of reaction is collected, together with partial collection of the product dichloropropanols, by distillation at reduced pressure, located always downstream the individual reaction zones of the cascade, and the distillation residue is fed into the next zone of the cascade.

21. The method according to claim 20, wherein the reaction mixture exiting from the last step of the cascade is subjected to a two-step distillation, wherein in the first step the water of reaction is separated together with the dichloropropanol reaction product as the distillate and in the second step the higher boiling waste products are separated as the distillation residue and the dichloropropanols and monochloropropanediols are separated as the distillate and are recycled back to the process, preferably into the first step of the cascade.

* * * * *